United States Patent
McMahon

(10) Patent No.: US 10,314,685 B2
(45) Date of Patent: Jun. 11, 2019

(54) SILICONE REFLUX VALVE FOR POLYMERIC STENTS

(71) Applicant: Boston Scientific Scimed, Inc., Maple Grove, MN (US)

(72) Inventor: Shane McMahon, Peterswell (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 172 days.

(21) Appl. No.: 14/450,790

(22) Filed: Aug. 4, 2014

(65) Prior Publication Data
US 2015/0045908 A1 Feb. 12, 2015

Related U.S. Application Data

(60) Provisional application No. 61/863,149, filed on Aug. 7, 2013.

(51) Int. Cl.
*A61F 2/04* (2013.01)
*A61F 2/90* (2013.01)

(52) U.S. Cl.
CPC ............... *A61F 2/04* (2013.01); *A61F 2/90* (2013.01); *A61F 2002/044* (2013.01)

(58) Field of Classification Search
CPC .... A61F 5/0036; A61F 2002/828; A61F 2/07; A61F 2/82; A61F 2/844
See application file for complete search history.

(56) References Cited

U.S. PATENT DOCUMENTS

| | | | |
|---|---|---|---|
| 6,302,917 B1 | 10/2001 | Dua et al. | |
| 6,305,436 B1 * | 10/2001 | Andersen | A61F 2/90 140/107 |
| 6,440,164 B1 * | 8/2002 | DiMatteo | A61F 2/2412 623/1.24 |
| 7,981,163 B2 | 7/2011 | Meade et al. | |
| 7,993,410 B2 | 8/2011 | Shin et al. | |
| 8,096,966 B2 | 1/2012 | Levine et al. | |
| 8,221,505 B2 | 7/2012 | Skerven | |
| 2003/0023303 A1 * | 1/2003 | Palmaz | A61F 2/2418 623/2.18 |
| 2003/0069646 A1 * | 4/2003 | Stinson | A61F 2/04 623/23.7 |
| 2003/0208261 A1 * | 11/2003 | Thorpe | A61F 2/2418 623/1.16 |

(Continued)

FOREIGN PATENT DOCUMENTS

| | | |
|---|---|---|
| CN | 2595394 Y | 12/2003 |
| WO | 2003030782 A1 | 4/2003 |
| WO | 2009153768 | 12/2009 |

OTHER PUBLICATIONS

PCT International Search Report, PCT International Application No. PCT/US2014/049587 (Filing Date: Aug. 4, 2014); dated Oct. 23, 2014; 4 pgs.

(Continued)

*Primary Examiner* — Ann Schillinger

(74) *Attorney, Agent, or Firm* — Seager, Tufte & Wickhem, LLP

(57) ABSTRACT

An anti-reflux valve having a mesh scaffolding and a valve extending from the mesh scaffolding, the valve supported by a loop. The loop can be formed by a filament extending from the mesh scaffolding or by a loop filament separate from the filament(s) forming the mesh scaffolding.

17 Claims, 3 Drawing Sheets

(56) References Cited

U.S. PATENT DOCUMENTS

| | | | |
|---|---|---|---|
| 2004/0102855 A1* | 5/2004 | Shank | A61F 2/90 |
| | | | 623/23.68 |
| 2005/0049718 A1 | 3/2005 | Dann et al. | |
| 2006/0212052 A1 | 9/2006 | Shin et al. | |
| 2006/0224183 A1* | 10/2006 | Freudenthal | A61B 17/0057 |
| | | | 606/213 |
| 2006/0241745 A1* | 10/2006 | Solem | A61F 2/246 |
| | | | 623/2.18 |
| 2007/0219610 A1* | 9/2007 | Israel | A61F 2/82 |
| | | | 623/1.11 |
| 2009/0177270 A1* | 7/2009 | Agnew | A61F 2/2418 |
| | | | 623/1.24 |
| 2011/0071613 A1 | 3/2011 | Wood et al. | |
| 2011/0098802 A1* | 4/2011 | Braido | A61F 2/2412 |
| | | | 623/1.26 |
| 2012/0259407 A1 | 10/2012 | Clerc et al. | |

OTHER PUBLICATIONS

PCT Written Opinion of the International Searching Authority, PCT International Application No. PCT/US2014/049587 (Filing Date: Aug. 4, 2014); dated Oct. 23, 2014; 6 pgs.

* cited by examiner

SILICONE REFLUX VALVE FOR POLYMERIC STENTS

CROSS-REFERENCE TO RELATED APPLICATIONS

This application claims the benefit of U.S. Provisional Application No. 61/863149, filed Aug. 7, 2013.

BACKGROUND

Patients presenting with refractory benign esophageal, biliary, colonic, and duodenal strictures, perforations, and leaks often suffer from symptoms of reflux. This can cause a lot of discomfort to the patient. The addition of an anti-reflux valve may help reduce this discomfort by preventing bile from travelling up through the esophagus, while allowing food to travel through the valve by peristaltic motion which moves food towards the stomach.

Without limiting the scope of the disclosure a brief summary of some of several embodiments is set forth below. Additional details of these embodiments of the disclosure and/or additional embodiments may be found in the Detailed Description below.

SUMMARY

In at least one embodiment, the anti-reflux valve has a mesh scaffolding and a valve extending from the mesh scaffolding and supported by a loop. In some embodiments, the loop is formed by a filament extending from the mesh scaffolding. In other embodiments, the loop is formed by a loop filament separate from the filament(s) forming the mesh scaffolding.

These and other embodiments which characterize the disclosure are pointed out with particularity in the claims annexed hereto and forming a part hereof. However, for further understanding of the disclosure reference can be made to the drawings which form a further part hereof and the accompanying descriptive matter, in which there is illustrated and described embodiments of the disclosure.

DESCRIPTION OF THE DRAWINGS

A detailed description of the disclosure is hereafter described with specific reference being made to the drawings.

FIGS. 1 and 1A are schematic views of an anti-reflux valve.

DETAILED DESCRIPTION

Figure 1:
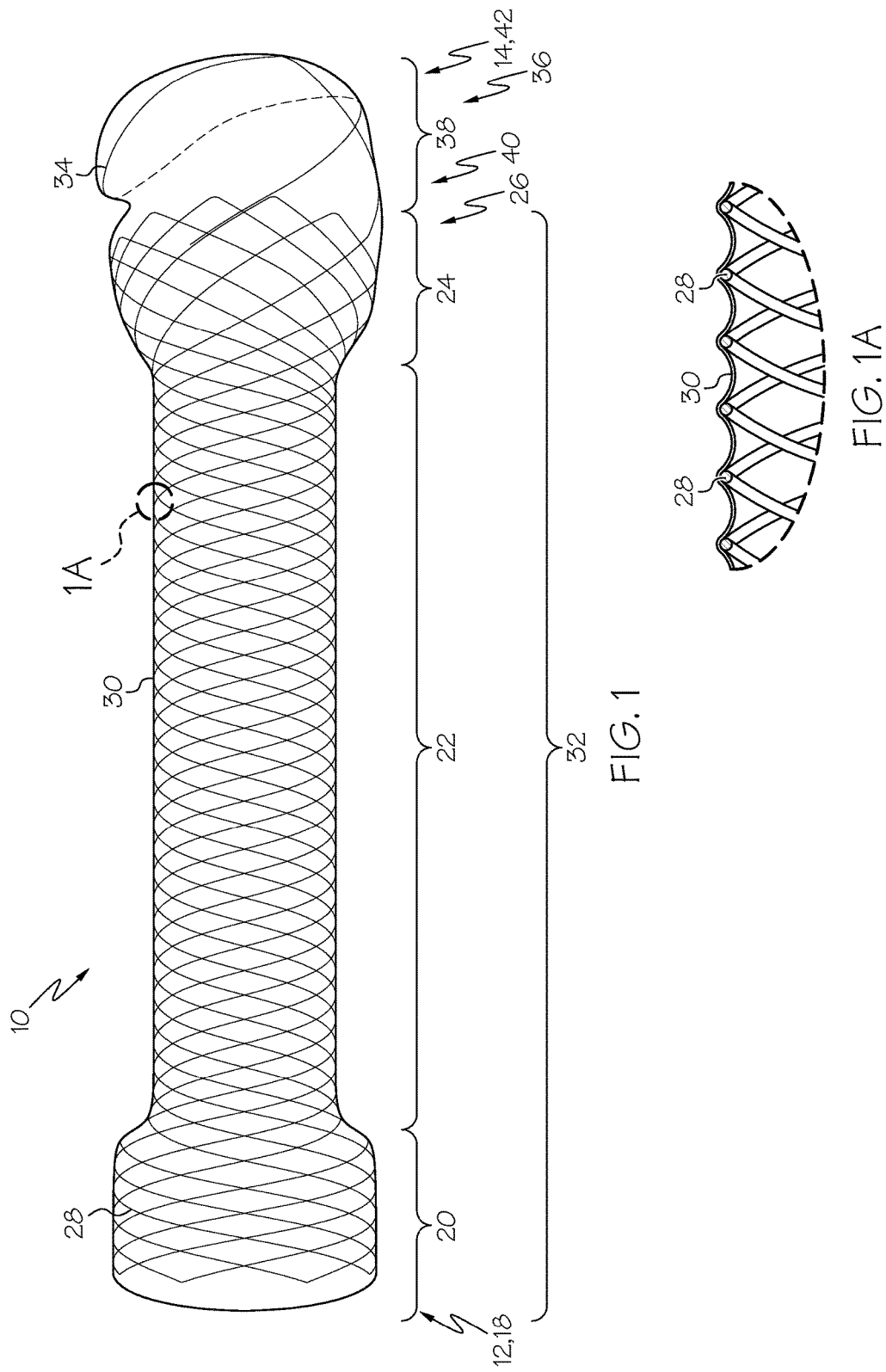

While this disclosure may be embodied in many different forms, there are described in detail herein specific embodiments of the disclosure. This description is an exemplification of the principles of the disclosure and is not intended to limit the disclosure to the particular embodiments illustrated.

For the purposes of this disclosure, like reference numerals in the figures shall refer to like features unless otherwise indicated.

As used herein the reference point for "proximal" and "distal" is the mouth or beginning of the gastrointestinal tract, with the "proximal" end of the anti-reflux valve 10 configured to be positioned closer to the beginning of the gastrointestinal tract than the "distal" end of the anti-reflux valve when the anti-reflux valve is implanted in the gastrointestinal tract.

As used herein a "section" has a longitudinal length and includes the entirety of the circumference.

As used herein an "oblique angle" includes 90 degrees.

A. Anti-Reflux Valve

In some embodiments the anti-reflux valve 10 includes a proximal valve end 12, a distal valve end 14, a mesh scaffolding 16 formed by at least one filament 28, and a valve 36 supported by a loop 34. In other embodiments, the anti-reflux valve 10 comprises a mesh scaffolding section 32 and a valve section 38 extending longitudinally from the mesh scaffolding section 32. In some embodiments, the mesh scaffolding section 32 comprises the mesh scaffolding 16 and a covering 30; and the valve section 38 comprises a portion of the covering 30 and the loop 34. In this embodiment, the mesh scaffolding section 32 forms the proximal valve end 12 and the valve section 38 forms the distal valve end 14. In one embodiment, the anti-reflux valve 10 has only one mesh scaffolding section 32 and only one valve section 38, where the valve section 38 extends longitudinally from the mesh scaffolding section. The mesh scaffolding 16, 32, the covering 30, and the valve 36 with loop 34 are discussed below in greater detail.

As can be seen in FIG. 1, the mesh scaffolding 16 and the valve 36 are tubular and define a lumen for the anti-reflux valve 10. Also as shown in FIG. 1, the mesh scaffolding 16 forms the proximal valve end 12 and the valve 36 forms the distal valve end 14.

The anti-reflux valve 10 can be sized for implantation in the esophagus, the colon, the duodenum, or the biliary tract of a patient, depending on the location of the stricture, perforations, and/or leaks. In at least one embodiment, the anti-reflux valve 10 conforms to the interior surface of the esophagus when implanted, expanding and contracting with the expansion and contraction of the esophagus.

The anti-reflux valve 10 has a longitudinal length measured from the proximal valve end 12 to the distal valve end 14. The longitudinal length of the anti-reflux valve 10 depends on the longitudinal length of the mesh scaffolding 16 and on the longitudinal length of the valve 36 which are discussed below in greater detail. In at least one embodiment, the longitudinal length of the anti-reflux valve 10 is about 90 mm to about 230 mm. Thus, in some embodiments the anti-reflux valve 10 has a maximum longitudinal length of 90 mm, in other embodiments the anti-reflux valve has a maximum longitudinal length of 190 mm, and in still other embodiments, the anti-reflux valve has a maximum longitudinal length of 230 mm.

In at least one embodiment, the anti-reflux valve is delivered to a desired implantation site by a delivery catheter. In some embodiments, the anti-reflux valve 10 is radially expandable from a delivery configuration to an implanted configuration. In some embodiments, the proximal valve end includes a retrieval loop (not shown) to aid in removing the anti-reflux valve from an implantation site.

In at least one embodiment the anti-reflux valve 10, the delivery system or other portion of the assembly may include one or more areas, bands, coatings, members, etc. that is (are) detectable by imaging modalities such as X-Ray, MRI, ultrasound, etc. In some embodiments at least a portion of the anti-reflux valve 10 and/or adjacent assembly is at least partially radiopaque.

In some embodiments the at least a portion of the anti-reflux valve 10 is configured to include one or more mechanisms for the delivery of a therapeutic agent. Often the agent will be in the form of a coating or other layer (or layers) of material placed on a surface region of the anti-reflux valve 10, which is adapted to be released at the site of implantation or areas adjacent thereto. As used herein the covering material 30 and the coating of therapeutic agent are different coatings.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof Where the therapeutic agent includes a polymer agent, the polymer agent may be a polystyrene-polyisobutylene-polystyrene triblock copolymer (SIBS), polyethylene oxide, silicone rubber and/or any other suitable substrate.

i. Mesh Scaffolding

A mesh scaffolding 16 is shown for example in FIG. 1. As noted above, the mesh scaffolding 16 forms a part of the mesh scaffolding section 32 of the anti-reflux valve 10. Suitable materials for the mesh scaffolding 16 are discussed below.

In some embodiments, the mesh scaffolding 16 is formed by a single filament 28. In other embodiments, the mesh scaffolding 16 is formed by a plurality of filaments 28. Hereinafter "filament" refers to a single filament or a plurality of filaments. In one embodiment, the filament 28 is a single filament (a monofilament). In another embodiment, the filament 28 is a multifilament. In one embodiment, the filament 28 has a diameter of 0.3-0.4 mm. In some embodiments, the filament 28 is interwoven for example by braiding, weaving, or knitting to form the mesh scaffolding 16. In at least one embodiment, the mesh scaffolding 16 defines a plurality of openings or meshes.

The mesh scaffolding 16 has a proximal scaffolding end 18 and a distal scaffolding end 26. In some embodiments, the mesh scaffolding 16 has a longitudinal length measured from the proximal scaffolding end 18 to the distal scaffolding end 26 of about 60-150 mm. Thus, in one embodiment, the mesh scaffolding 16 has a maximum longitudinal length of 60 mm, and in another embodiment the mesh scaffolding 16 has a maximum longitudinal length of 150 mm. In at least one embodiment, the mesh scaffolding 16 has a plurality of turns at the proximal scaffolding end 18 and a plurality of turns at the distal scaffolding end 26. In some embodiments, the turns at the scaffolding ends 18, 26 provide the mesh scaffolding 16 with atraumatic ends. In one embodiment, the end of the filament forming the mesh scaffolding is positioned between the scaffolding ends 18, 26 to provide the mesh scaffolding with atraumatic ends.

In at least one embodiment, the mesh scaffolding 16 has a proximal scaffolding end region 20, a distal scaffolding end region 24, and a scaffolding medial region 22 extending between and connecting the two scaffolding end regions 20,24. As discussed above, in some embodiments the anti-reflux valve 10 is implanted in the esophagus. In these embodiments, the mesh scaffolding 16 has a diameter of 15-20 mm. In some embodiments, the proximal scaffolding end region 20 and the distal scaffolding end region 24 are flared so that the diameters of the proximal and distal scaffolding end regions 20, 24 are greater than the diameter of the scaffolding medial region 22. In at least one embodiment the diameter of the proximal scaffolding end region 20 is about 17% greater than the diameter of the scaffolding medial region 22 and the diameter of the distal scaffolding end region 24 is at most 17% greater than the diameter of the scaffolding medial region 22. In some embodiments, the diameters of the scaffolding end regions 20, 24 are at most 10% greater than the diameter of the scaffolding medial region 22. In other embodiments the diameters of the scaffolding end regions 20, 24 are at most 5% greater than the diameter of the scaffolding medial region 22.

ii. Covering

In some embodiments, the outer surface of the mesh scaffolding 16 is fully covered by covering material 30 so that the covering material 30 extends from the proximal scaffolding end 18 to the distal scaffolding end 26. Thus, as can be seen in FIG. 1, the covering material occludes all of the meshes defined by the mesh scaffolding 16. In other embodiments, only a portion of the longitudinal length of the mesh scaffolding 16 is covered with covering material 30 (not shown). As a non-limiting example, a proximal portion of the mesh scaffolding 16 is not covered with covering material 30 while the distal portion of the mesh scaffolding 16 is covered with covering material 30. Thus, in this embodiment, only some of the meshes defined by the mesh scaffolding 16 are occluded by the covering material 30. For either embodiment, the covering material 30 forms a part of the mesh scaffolding section 32, as noted above.

In at least one embodiment the covering material 30 is a sleeve. In at some embodiments, the covering material 30 provides for a smooth outer surface for the mesh scaffolding 16. In other embodiments, the outer surface is not smooth. For example, an uneven or rough outer surface can be due to the mesh scaffolding being thicker than the covering material. This is shown for example in FIG. 1A.

In some embodiments, the outer surface of the anti-reflux valve 10 is formed entirely by the covering 30, and the inner surface of the anti-reflux valve 10 is formed in part by the covering 30 and in part by the mesh scaffolding 16. In this embodiment, the covering 30 has a longitudinal length equal to the longitudinal length of the anti-reflux valve 10.

In a further aspect the mesh scaffolding 16 has a covering on an interior surface (not shown). The interior covering has a maximum longitudinal length equal to the longitudinal length of the mesh scaffolding 16. In this embodiment, the outer surface of the anti-reflux valve 10 is formed entirely by the covering 30, and the inner surface of the anti-reflux valve 10 is formed in part by an interior cover of the mesh scaffolding. For embodiments, where the covering 30 forms the valve 36, the inner surface of the anti-reflux valve 10 is further formed in part by the covering 30.

In at least one embodiment, the covering 30 has a longitudinal length of about 60-190 mm. Thus, in some embodiments the covering 30 has a maximum longitudinal length of 60 mm; in other embodiments, the covering has a maximum longitudinal length of 100 mm; in still other embodiments, the covering has a maximum longitudinal length of 190 mm; in yet additional embodiments, the covering has a maximum longitudinal length of 230 mm. In some embodiments, the covering 30 has a thickness of at least 3-4 mm. Suitable materials for the covering 30 are discussed below.

iii. Valve

The valve 36 extends longitudinally from the distal scaffolding end 26 to the distal valve end 14. The valve 36 has a proximal valve end 40 and a distal valve end 42. The valve 36 forms a part of a valve section 38 of the anti-reflux valve 10. In some embodiments, the valve 36 has a variable diameter. In other embodiments, the valve 36 has a non-cylindrical shape.

In at least one embodiment, the valve 36 is formed by a portion of the covering material 30 extending beyond the distal scaffolding end 26. In some embodiments, the covering material 30 forming the valve 36 is the same as the material covering the mesh scaffolding 16. In this embodiment, the covering material 30 has a longitudinal length equal to the longitudinal length of the anti-reflux valve 10. In other embodiments, a first covering made of covering material 30, covers the mesh scaffolding 16 and a second covering/sleeve made of a different covering material is attached to and extends from the mesh scaffolding 16 to form the valve 36 (not shown). In this embodiment, both coverings have a longitudinal length less than the longitudinal length of the anti-reflux valve 10.

As noted above, the valve 36 includes a loop 34. In at least one embodiment, the loop 34 facilitates opening of the valve 36 for consuming food. Without being bound by theory, when the anti-reflux valve 10 is implanted, the valve 36 expands during peristalsis thereby allowing food to pass through the valve 36. The loop 34 provides scaffolding structure that aids in forming the diameter of the valve for food to pass through the valve 36. Since there is a single loop 34 providing support to the valve 36, the radial force provided by the loop 34 allows the valve 36 to collapse under normal esophageal conditions while acting as a spring during peristalsis to allow the valve to open to the diameter of the esophageal lumen. Thus, the loop 34 supports the opening of the valve during peristalsis and reduces the opportunity of blockage of the valve during peristalsis.

In some embodiments, a portion of a filament 28 forming the mesh scaffolding 16 exits and re-enters the distal scaffolding end 26 to form the loop 34. In some embodiments, where a plurality of filaments 28 is interwoven form the mesh scaffolding 16, one of the filaments 28 has a greater length in order to form the loop 34. The length of the filament 28 forming the loop 34 is dependent at least on the diameter of the loop 34 and the distance between the loop 34 and the distal scaffolding end 26.

In at least one embodiment, the filament forming the loop 34 is secured to the mesh scaffolding 16 by being interwoven into the mesh scaffolding 16. In some embodiments, each portion of the filament forming the loop 34 that is interwoven into the mesh scaffolding 16 is parallel to a filament forming the mesh scaffolding 16. In at least one embodiment, the filament forming the loop 34 is also bonded to the mesh scaffolding 16. In one embodiment, the covering material 30 bonds the filament forming the loop 34 to the mesh scaffolding 16. FIG. 1 shows the filament interwoven into, and bonded to, the mesh scaffolding 16 by covering material 30.

In one embodiment, the positions where the filament exits and re-enters the mesh scaffolding 16 are 180 degrees apart. In other words, the exit and re-entry points of the filament to the mesh scaffolding 16 are opposite one another.

In other embodiments, a loop filament, that is separate from the filaments 28 forming the mesh scaffolding, forms the loop 34. Thus, in this embodiment, the loop filament is a separate, different member from the mesh filament 28. For this embodiment, the end regions of the loop filament are secured to the mesh scaffolding 16 and the medial region of the loop filament forms the loop 34. The end regions of the loop filament extend from the cross-over of the loop filament to the mesh scaffolding 16. The end regions of the loop filament can be secured to the mesh scaffolding 16 as discussed above for a filament 28 forming the loop 34. In one embodiment, the loop filament is made of a different material than the filament 28. As discussed above with regard to the filament 28, the loop filament has a diameter of 0.3-0.4 mm and is either a single filament (a monofilament) or a multifilament.

Figure 2:
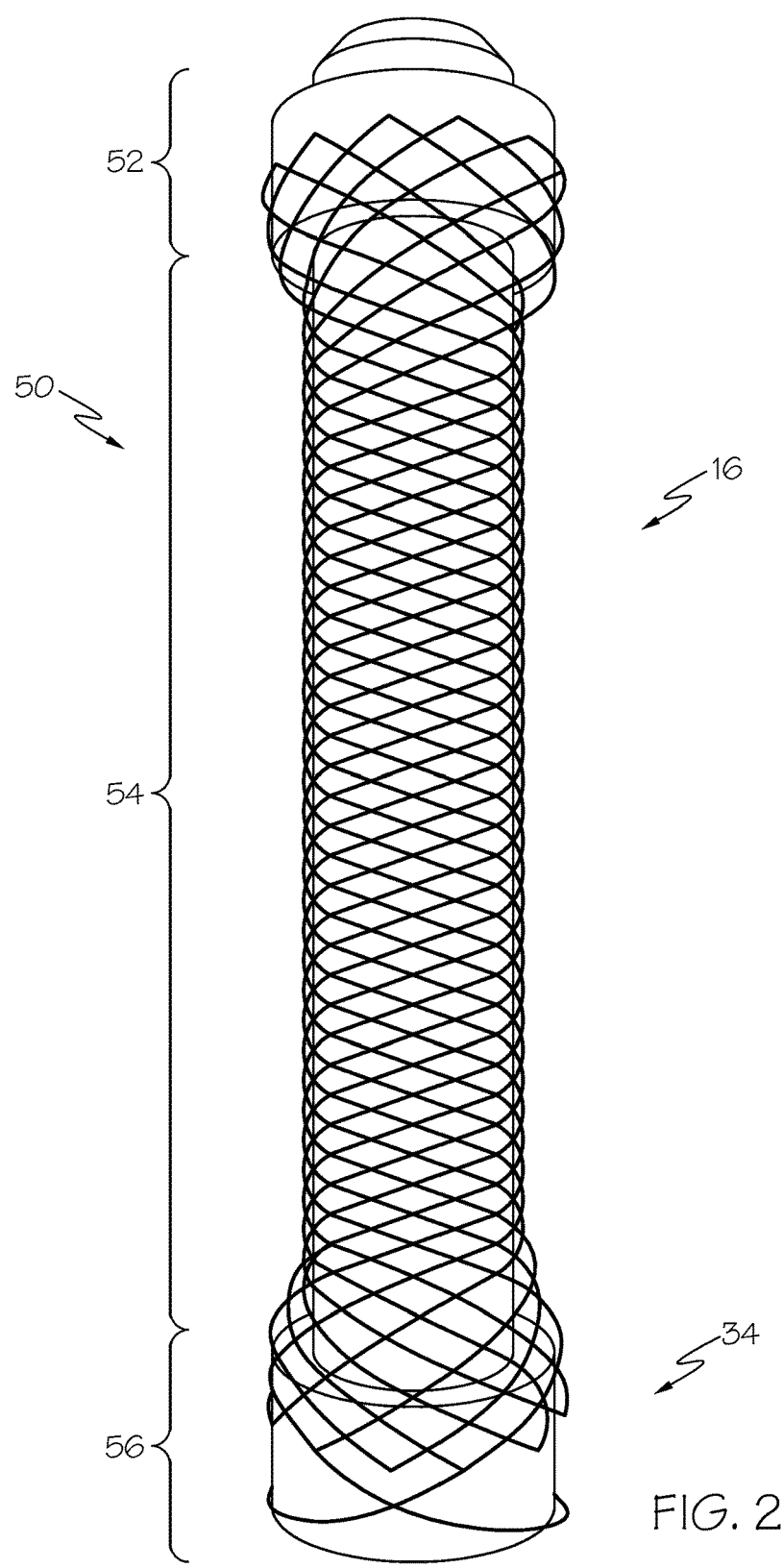
FIGS. 2-3 are schematic views of an anti-reflux valve on a mandrel.
Figure 3:
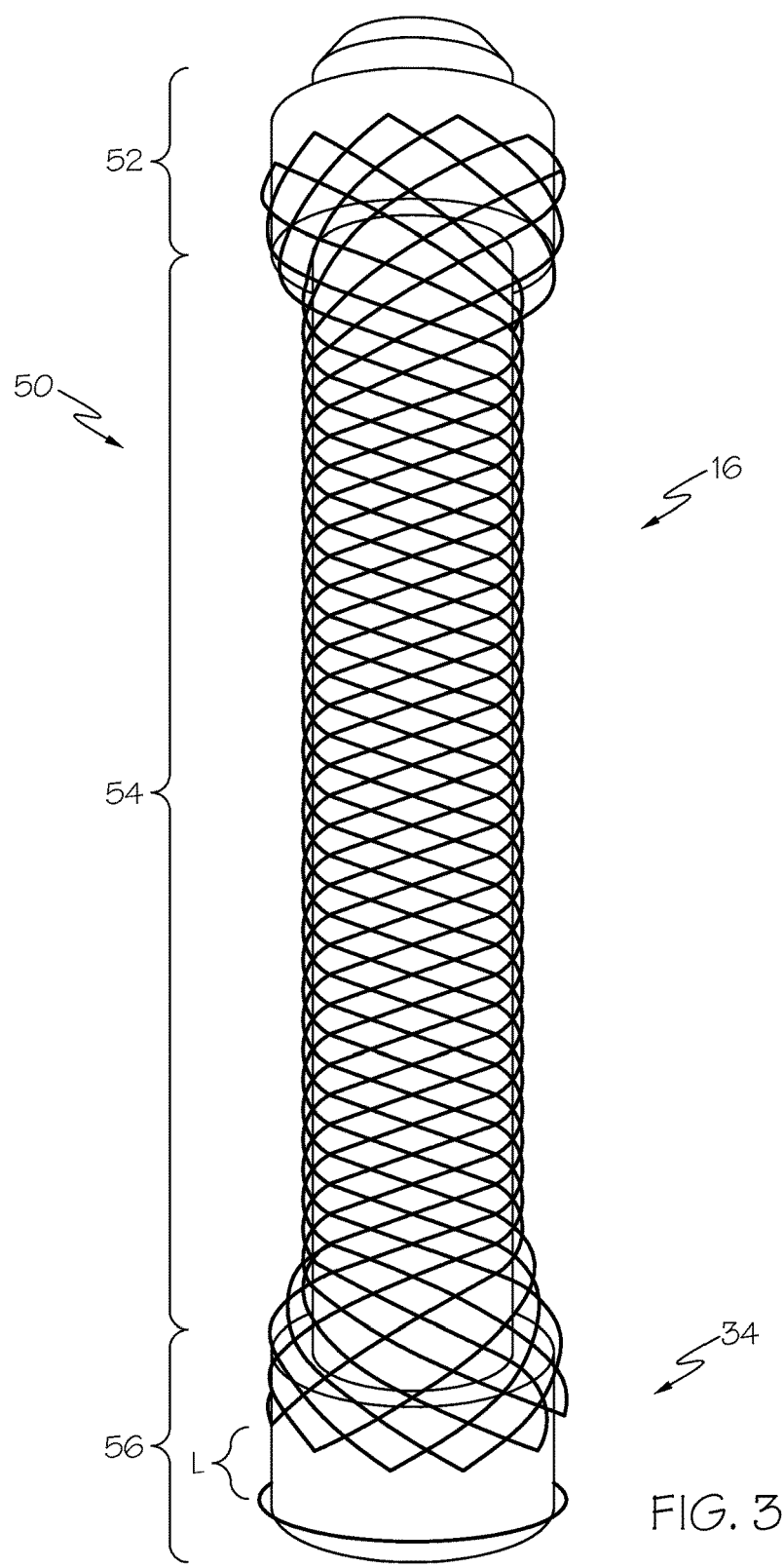

In at least one embodiment, the loop 34 is affixed to the covering material forming the valve 36. In some embodiments, the loop 34 supports the valve 36. As can be seen in the figures, the loop 34 is a single loop. In other words, the filament forming the loop 34 has a single cross-over, as shown for example in FIGS. 1-3. In one embodiment the single cross-over is positioned between the distal scaffolding end 26 and the distal valve end 14. In at least one embodiment the filament forming the loop 34 has a diameter of 0.3-0.4 mm. Suitable materials for the valve 36 and loop 34 are discussed below. In some embodiments, the loop 34 is detectable by imaging modalities such as X-Ray, MRI, ultrasound, etc. In one embodiment, the loop 34 is radiopaque.

In at least one embodiment, the loop 34 has a longitudinal length (L) measured from where the loop 34 exits the mesh scaffolding 16 to the greatest longitudinal extent of the loop 34. In some embodiments, the longitudinal length of the loop 34 is about 30-40 mm. In at least one embodiment the loop 34 has a maximum diameter equal to the diameter of the distal scaffolding end region 24. In at least one embodiment, the loop 34 is at an oblique angle to the longitudinal axis of the anti-reflux valve 10.

In some embodiments, the longitudinal length of the loop 34 is substantially equal to the longitudinal length of the valve 36, as shown for example in FIG. 1. For these embodiments, the valve 36 has a longitudinal length measured from the proximal valve end 40 to the distal valve end 42 of about 30-40 mm. Thus, in some embodiments, the valve 36 has a maximum longitudinal length of 30 mm, and in other embodiments, the valve 36 has a maximum longitudinal length of 40 mm.

In other embodiments, the material 30 forming the valve 36 extends 30-40 mm beyond the loop 34 (not shown). For these embodiments, the valve 36 has a longitudinal length measured from the proximal valve end 40 to the distal valve end 42 of about 60-80 mm. Thus, in some embodiments, the valve 36 has a maximum longitudinal length of 60 mm, and in other embodiments the valve 36 has a maximum longitudinal length of 80 mm.

B. Forming the Anti-Reflux Valve

In at least one embodiment, an anti-reflux valve 10 as described above is formed by a combination of at least some of the following steps:

1) Forming a Mesh Scaffolding 16.

In some embodiments, forming the mesh scaffolding 16 comprises interweaving a single filament 28 or a plurality of filaments 28; and forming a loop 34 by extending the single filament 28, or one of the plurality of filaments 28, beyond the distal scaffolding end 26 and interweaving the loop filament into the mesh scaffolding 16.

In other embodiments, forming the mesh scaffolding 16 comprises interweaving a single filament 28 or a plurality of filaments 28; forming a loop 34 from a loop filament where end regions of the loop filament are secured to the mesh scaffolding 16 and a medial region of the loop filament forms the loop 34.

In at least one embodiment, the mesh scaffolding 16 is formed on a mandrel 50. In some embodiments, the mandrel 50 has a first mandrel end region 52, a mandrel medial region 54 and a second mandrel end region 56. In at least one embodiment, the first and second mandrel end regions 52, 56 have a greater diameter than the mandrel medial region 54. In some embodiments, the mandrel 50 has a diameter of 15-20 mm. In some embodiments, the first and second mandrel end regions 52, 56 are flared so that the diameters of the first and second mandrel end regions 52, 56 are greater than the diameter of the mandrel medial region 54. In at least one embodiment the diameter of the first mandrel end region 52 is about 17% greater than the diameter of the mandrel medial region 54 and the diameter of the second mandrel end region 56 is at most 17% greater than the diameter of the mandrel medial region 54. In some embodiments, the diameters of the mandrel end regions 52, 56 are at most 10% greater than the diameter of the mandrel medial region 54. In other embodiments the diameters of the mandrel end regions 52, 56 are at most 5% greater than the diameter of the mandrel medial region 54.

In at least one embodiment, the second mandrel end region 56 has a longitudinal length that is sufficiently long to form a valve 36, 38 having a desired longitudinal length. In at least one embodiment, the mandrel 50 has a smooth outer surface.

In one embodiment, the filament 28 is braided in a one under one over pattern.

The mesh scaffolding 16 may alternatively be created by cutting or etching a design from a tubular stock, from a flat sheet which is cut or etched and which is subsequently rolled. Any other suitable technique which is known in the art or which is subsequently developed may also be used to manufacture the mesh scaffolding 16 disclosed herein.

2) Coating the Mesh Scaffolding 16 with a Covering Material 30.

In at least one embodiment, the mesh scaffolding 16 is coated while positioned on the mandrel 50. In some embodiments, the mesh scaffolding 16 is fully covered with the covering material 16. In one embodiment, the covering material 30 bonds the loop 34 to the mesh scaffolding 16.

The covering material 30 can be applied to the mesh scaffolding 16 in any suitable manner.

3) Forming the Valve 36.

In at least one embodiment, the valve 36 is formed when the mesh scaffolding 16 and loop 34 are positioned on the mandrel 50.

In some embodiments, the valve 36 is formed by applying the covering material 30 beyond the distal scaffolding end 26 to cover the loop 34, thereby forming the valve 36.

In other embodiments, the valve 36 is formed by applying a second covering material to the mesh scaffolding so that it bonds to the covering material 30 covering the mesh scaffolding and applying the second covering material so that it extends beyond the distal scaffolding end to cover the loop, thereby forming the valve.

C. Suitable Materials

The filament(s) 28 and/or the loop filament may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyethylene terephthalate (PET), thermoplastic polymers, polyester, and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The filament(s) 28 and/or the loop filament may be made of materials with shape memory effect, such as Nitinol; may be made of materials with superelastic properties, such as Nitinol; or may be made of materials which are plastically deformable. In the case of materials with shape memory effect, the mesh scaffolding 16 may be provided with a memorized shape and then deformed to a reduced diameter shape. The mesh scaffolding 16 may restore itself to its memorized shape upon being heated to a transition temperature and having any restraints removed therefrom.

Suitable materials for the valve 36 and/or the covering material 30 include, but are not limited to: silicone, urethane, polyurethane, polyamides, and combinations thereof In some embodiments, silicone grade 4840/4830/4820 is used to coat the mesh scaffolding 16 and to form the valve 36.

In at least one embodiment, the valve 36 is made of a first material and a second material different than the first material. In some embodiments, the first material is silicone and the second material is polyethylene terephthalate (PET). In one embodiment, a sleeve 30 is formed by the first material and a loop 34 is formed by the second material.

The embodiments or aspects of the anti-reflux valve 10, including the embodiments presented in the claims, may be combined in any fashion and combination and be within the scope of the present disclosure. As a non-limiting example, the following embodiments or aspects of the anti-reflux valve 10 may be combined in any fashion and combination and be within the scope of an anti-reflux valve 10 disclosed herein, as follows:

Aspect 1: An anti-reflux valve (10) comprising:
a filament (28), the filament forming:
a mesh scaffolding (16) with a distal scaffolding end (26); and
a loop (34) extending a distance from the distal scaffolding end, the loop forming a part of a valve (36).

Aspect 2: An anti-reflux valve (10) comprising:
a mesh scaffolding section (32) comprising:
a filament (28) forming a mesh scaffolding (16) with a distal scaffolding end (26) forming an end of the mesh scaffolding section;
a covering (30);
a valve section (38) extending from the mesh scaffolding section (16), the valve section comprising:
a valve (36), wherein the valve is an extension of the covering (30), the valve further including a loop (34) extending a distance the distal scaffolding end (26).

Aspect 3. An anti-reflux valve (10) comprising:
a valve (36) extending longitudinally from a support (16), characterized in that the valve includes a loop (34).

Aspect 4. An anti-reflux valve (10) comprising a sleeve of first material (30) and a loop of second material (34) different than the first material, the loop (34) affixed into the sleeve of first material (30).

Aspect 5. A method of forming an anti-reflux valve (10) comprising:
forming a mesh scaffolding (16) from a filament (28), the filament further
forming a loop (34) extending a distance from a distal scaffolding end (26); and
forming a valve (36) from a polymeric material (30), the valve extending from the mesh scaffolding (16) and including the loop (34).

Aspect 6. A method of forming an anti-reflux valve (10) comprising:
forming a mesh scaffolding section (32);
forming a valve section (38), the valve section extending longitudinally from the mesh scaffolding section, the valve section comprising a valve (36) with a loop (34) formed by a filament (28) extending from the mesh scaffolding section.

Aspect 7. A method of forming an anti-reflux valve (10) comprising:
forming a valve (36), the valve comprising a sleeve of first material (30) and a loop of second material (34) different than the first material.

Aspect 8. The method of aspect 7, further comprising securing the valve (36) to an end of a support (16).

Aspect 9. The anti-reflux valve as recited in aspects 2 and 6, wherein the mesh scaffolding section (32) is formed on a mandrel (50).

Aspect 10. The anti-reflux valve as recited in aspects 2, 6, and 9, wherein the valve section (38) is formed on the mandrel (50).

Aspect 11. The anti-reflux valve as recited in aspects 1-8, wherein the anti-reflux valve (10) is formed on a mandrel (50).

Aspect 12. The anti-reflux valve as recited in aspects 9-11, wherein the mandrel (50) has a first mandrel end region (52), a mandrel medial region (54), and a second mandrel end region (56), wherein the mandrel medial region (54) has a smaller diameter than the first and second mandrel end regions (52, 56).

Aspect 13. The anti-reflux valve of aspect 12, wherein a diameter of the first mandrel end region (52) is at most 17% greater than a diameter of the mandrel medial region (54) and a diameter of the second mandrel end region (56) is at most 17% greater than a diameter of the mandrel medial region (54).

Aspect 14. The anti-reflux valve of aspects 12-13, wherein a diameter of the first mandrel region (52) is at most 10% greater than a diameter of the mandrel medial region (54), and a diameter of the second mandrel region (56) is at most 10% greater than a diameter of the mandrel medial region (54).

Aspect 15. The anti-reflux valve of aspects 12-14, wherein a diameter of the first mandrel region (52) is at most 5% greater than a diameter of the mandrel medial region (54), and a diameter of the second mandrel region (56) is at most 5% greater than a diameter of the mandrel medial region (54).

Aspect 16. The anti-reflux valve as recited in aspects 2, 6, and 9, wherein the mesh scaffolding section (32) is formed by interweaving a filament (28).

Aspect 17. The anti-reflux valve of aspects 6, and 9, wherein the mesh scaffolding section (32) comprises a filament (28) forming a mesh scaffolding (16) and a covering (30).

Aspect 18. The anti-reflux valve as recited in aspects 3 and 8, wherein the support is a mesh scaffolding (16).

Aspect 19. The anti-reflux valve of aspects 1-2, 5, and 17-18, wherein the mesh scaffolding (16) has flared scaffolding end regions (20, 24).

Aspect 20. The anti-reflux valve of aspect 19, wherein the mesh scaffolding (16) has a proximal scaffolding end region (20), a scaffolding medial region (22), and a distal scaffolding end region (24) wherein at least one of the scaffolding regions (20, 22, 24) has a smaller diameter than other of the scaffolding regions (20, 22, 24).

Aspect 21. The anti-reflux valve of aspect 20, wherein a diameter of the scaffolding end regions (20, 24) is at most 17% greater than a diameter of a scaffolding medial region (22).

Aspect 22. The anti-reflux valve of aspect 20-21, wherein the diameter of the scaffolding end regions (20, 24) is at most 10% greater than the diameter of the scaffolding medial region (22).

Aspect 23. The anti-reflux valve of aspects 20-22, wherein the diameter of the scaffolding end regions (20, 24) is at most 5% greater than the diameter of the scaffolding medial region (22).

Aspect 24. The anti-reflux valve of aspects 1-2, 5, and 17-23, wherein the filament (28) forming the mesh scaffolding (16) forms a plurality of turns at the proximal scaffolding end (18) and a plurality of turns at the distal scaffolding end (26) so that the proximal and distal scaffolding ends (18, 26) are atraumatic ends.

Aspect 25. The anti-reflux valve of aspects 1-2, 5, and 17-24, wherein the filament (28) forming the mesh scaffolding (16) comprises polyethylene terephthalate (PET).

Aspect 26. The anti-reflux valve of aspect 1-2, 5, and 17-25, wherein the filament (28) forming the mesh scaffolding (16) also forms the loop (34).

Aspect 27. The anti-reflux valve of aspects 1-2, 5, and 17-25, wherein the filament forming the loop (34) is not the filament (28) forming the mesh scaffolding (16).

Aspect 28. The anti-reflux valve of aspects 1-2, 5, and 17-27, wherein the mesh scaffolding (16) has a maximum longitudinal length of 150 mm.

Aspect 29. The anti-reflux valve of aspects 1-2, 5, and 17-28, wherein the mesh scaffolding (16) has a maximum longitudinal length of 60 mm.

Aspect 30. The anti-reflux valve of aspects 3, 8, and 18-29 wherein the loop (34) extends from the support (16).

Aspect 31. The anti-reflux valve of aspects 24-30, wherein the loop (34) is not one of the plurality of turns at the distal scaffolding end (26).

Aspect 32. The anti-reflux valve of aspects 2-4 and 7-31 wherein the loop (34) is a filament.

Aspect 33. The anti-reflux valve of aspects 1-32, wherein the loop (34) has a maximum longitudinal length of 40 mm.

Aspect 34. The anti-reflux valve of aspects 1-33, wherein the loop (34) has a maximum longitudinal length of 30 mm.

Aspect 35. The anti-reflux valve of aspect 32-34, wherein the filament (34) has a diameter of 0.3 to 0.4 mm.

Aspect 36. The anti-reflux valve of aspects 1-2, 5-6, 9-25, 27-28, and 31-35, the filament (28) being a plurality of filaments, wherein one of the plurality of filaments has a greater length to form the loop (34) and others of the plurality of filaments form the mesh scaffolding (16).

Aspect 37. The anti-reflux valve of aspects 1-2, 5-6, 9-25, 27-28, and 31-36, wherein the loop (34) is formed by a single filament.

Aspect 38. The anti-reflux valve of aspects 1-2, 5-6, 9-25, 27-28, and 31-37 wherein the filament (28, 34) is a single filament (monofilament).

Aspect 39. The anti-reflux valve of aspects 1-2, 5-6, 9-25, 27-28, and 31-38, wherein the loop (34) comprises a single cross-over of the filament (28).

Aspect 40. The anti-reflux valve of aspect 39, wherein the single cross-over is positioned between the distal scaffolding end (26) and a distal end (14) of the anti-reflux valve (10).

Aspect 41. The anti-reflux valve of aspects 1-2, 5-6, 9-25, 27-28, and 31-40, wherein the loop (34) comprises polyethylene terephthalate (PET).

Aspect 42. The anti-reflux valve of aspects 1-41, wherein the loop (34) is radiopaque.

Aspect 43. The anti-reflux valve of aspect 1-2, 5-6, 9-25, 27-28, and 35-42, wherein the filament (28, 34) has a diameter of 0.3 to 0.4 mm.

Aspect 44. The anti-reflux valve of aspects 1, 9, 19-28, 31-43, wherein the valve (36) is an extension of a covering (30) extending over the mesh scaffolding (16).

Aspect 45. The anti-reflux valve of aspect 55, wherein the covering (30) comprises silicone.

Aspect 46. The method of forming the anti-reflux valve of aspect 5, 19-28, and 31-43 wherein the polymeric material forming the valve (36) further covers the mesh scaffolding (16).

Aspect 47. The anti-reflux valve of aspects 5 and 29, wherein the polymeric material comprises silicone.

Aspect 48. The anti-reflux valve of aspect 47, wherein the silicone is selected from the group consisting of silicone grade 4840, silicone grade 4830, silicone grade 4820, and combinations thereof Aspect 49. The anti-reflux valve of aspects 1-48, wherein the anti-reflux valve (10) has a maximum longitudinal length of 190 mm.

Aspect 50. The anti-reflux valve of aspects 1-49, wherein the anti-reflux valve (10) has a maximum longitudinal length of 90 mm.

Aspect 51. The anti-reflux valve of aspects 1-50, wherein the anti-reflux valve (10) includes a coating of therapeutic agent.

Aspect 52. The anti-reflux valve of aspects 4, 7, 11-15, 31-35, 37-45, and 49-51 wherein the first material is silicone and the second material is polyethylene terephthalate (PET).

Aspect 53. The anti-reflux valve of aspect 52, wherein the silicone is selected from the group consisting of silicone grade 4840, silicone grade 4830, silicone grade 4820, and combinations thereof Aspect 54. The anti-reflux valve of aspects 52-53, wherein the sleeve of first material is supported only by the loop (34).

Aspect 55. The anti-reflux valve of aspects 52-54, an end of the sleeve of first material being secured to a support.

Aspect 56. The anti-reflux valve of aspect 55, wherein the support is a mesh scaffolding (16) as recited in aspects 18, 24-28, 31, 36, and 44.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

The invention claimed is:
1. An implantable valve device comprising:
a tubular mesh scaffolding comprising a plurality of filaments, the mesh scaffolding defining a lumen extending therethrough to a distal scaffolding end;
only one filament of the plurality of filaments extending distally a distance away from the distal scaffolding end and forming only a single loop, the single loop comprising only a single cross-over of the one filament;
a covering extending continuously along the mesh scaffolding, the single loop, and a valve section; and
the valve section extending distally beyond the distal scaffolding end, the valve section comprising:
a valve connected to, and extending longitudinally from, the mesh scaffolding, wherein the valve is an extension of the covering and comprises the single loop, the valve closing off the lumen of the mesh scaffolding;
wherein the valve section includes only the one filament of the plurality of filaments.

2. The valve device of claim 1, wherein the covering occludes openings defined by the mesh scaffolding.

3. The valve device of claim 1, wherein the filament comprises polyethylene terephthalate (PET) and the valve comprises silicone.

4. The valve device of claim 1, wherein the mesh scaffolding has a proximal scaffolding end region, a scaffolding medial region, and a distal scaffolding end region wherein the scaffolding medial region has a smaller diameter than the proximal and distal scaffolding end regions.

5. The valve device of claim 1, wherein the one filament of the plurality of filaments extending distally a distance away from the distal scaffolding end has a greater length to form the single loop.

6. The valve device of claim 1, wherein the single loop has a radial force allowing the valve to collapse closed under normal esophageal conditions, thereby closing the scaffolding lumen, and to then spring open during peristalsis.

7. An implantable valve device comprising:
a mesh scaffolding section comprising:
a filament forming a tubular mesh scaffolding defining a lumen extending therethrough to a distal scaffolding end, the distal scaffolding end being an end of the mesh scaffolding section;
a covering extending continuously over the mesh scaffolding and a valve section;
the valve section extending distally beyond the distal scaffolding end of the mesh scaffolding section, the valve section consisting of:
a valve closing off the lumen of the mesh scaffolding, wherein the valve is an extension of the covering; and
only a single loop, wherein the single loop is formed by the filament extending distally for a distance from the distal scaffolding end along the valve so that the single loop has a longitudinal length, wherein the single loop comprises only a single cross-over of the filament.

8. The valve device of claim 7, wherein the filament comprises polyethylene terephthalate (PET) and the valve comprises silicone.

9. The valve device of claim 7, wherein the mesh scaffolding has a proximal scaffolding end region, a scaffolding medial region, and a distal scaffolding end region wherein the scaffolding medial region has a smaller diameter than the proximal and distal scaffolding end regions.

10. The valve device of claim 7, wherein the filament is a plurality of filaments, and one of the plurality of filaments has a greater length to form the single loop.

11. The valve device of claim 7, wherein the filament is a single filament.

12. The valve device of claim 7, wherein the single loop has a radial force allowing the valve to collapse closed under normal esophageal conditions, thereby closing the scaffolding lumen, and to then spring open during peristalsis.

13. An implantable valve device comprising:
   a mesh scaffolding section comprising:
      a tubular mesh scaffolding including a filament, the tubular mesh scaffolding defining a lumen extending therethrough from a proximal end of the tubular mesh scaffolding to a distal end of the tubular mesh scaffolding;
   a valve section extending distally beyond the mesh scaffolding section, the valve section consisting of:
      only a single loop of the filament extending distally beyond the distal end of the mesh scaffolding, wherein the single loop comprises only a single cross-over of the filament; and
   a covering extending continuously along the mesh scaffolding and the valve section, wherein the covering defines a valve having an opening sized and configured for food to pass therethrough, the valve extending longitudinally and distally from the distal end of the mesh scaffolding, wherein the single loop has a spring radial force allowing the valve to move between an open state, allowing food to pass therethrough during peristalsis, to a collapsed state, thereby closing the scaffolding lumen.

14. The valve device of claim 13, wherein the covering occludes openings defined by the mesh scaffolding.

15. The valve device of claim 13, wherein the covering extends over an entirety of an inner surface of the mesh scaffolding.

16. The valve device of claim 13, wherein the mesh scaffolding has a proximal scaffolding end region, a scaffolding medial region, and a distal scaffolding end region wherein the scaffolding medial region has a smaller diameter than the proximal and distal scaffolding end regions.

17. The valve device of claim 13, wherein the single loop extends along the opening of the valve.

* * * * *